United States Patent [19]

Kastrubin et al.

[11] 4,383,522
[45] May 17, 1983

[54] METHOD OF ELECTROANESTHESIA

[76] Inventors: Eduard M. Kastrubin, Frunzenskaya naberezhnaya, 36, kv. 105; Jury V. Kordjukov, Nogatinskaya ulitsa, 13, korpus 1, kv. 43, both of Moscow, U.S.S.R.

[21] Appl. No.: 205,981

[22] Filed: Nov. 12, 1980

[51] Int. Cl.³ .............................................. A61N 1/34
[52] U.S. Cl. .................................................. 128/1 C
[58] Field of Search ........... 128/1 C, 731, 732, 420 P, 128/420 R

[56] References Cited

U.S. PATENT DOCUMENTS

| | | | |
|---|---|---|---|
| 3,989,051 | 11/1976 | Nozhnikov et al. | 128/1 C |
| 4,018,218 | 4/1977 | Carlson | 128/1 C |
| 4,140,133 | 2/1979 | Kastrubin et al. | 128/1 C |
| 4,153,061 | 5/1979 | Nemec | 128/420 A |

FOREIGN PATENT DOCUMENTS

| | | | |
|---|---|---|---|
| 467502 | 6/1937 | United Kingdom | 128/420 A |
| 972926 | 10/1964 | United Kingdom | 128/1 C |
| 454916 | 12/1974 | U.S.S.R. | |

OTHER PUBLICATIONS

Persianinov et al.; "Experimental Surgery and Anesthesia;" No. 4, 1975, p. 74.

*Primary Examiner*—William E. Kamm
*Attorney, Agent, or Firm*—Fleit, Jacobson & Cohn

[57] ABSTRACT

Described herein is a method of electroanesthesia, which provides for preliminary preoperative medication of a patient, carrying out induction anesthesia, administering muscle relaxants and intubation followed by forced pulmonary ventilation. Electroanesthesia is performed using D.C. pulses in combination with an additional constant component, the repetition frequency of said pulses being controllable. Used as said pulses are stabilized voltage pulses having the same amplitude and a difference between the repetition frequency within a range of about 100 to about 200 Hz at a constant or variable pulses ratio.

4 Claims, 1 Drawing Figure

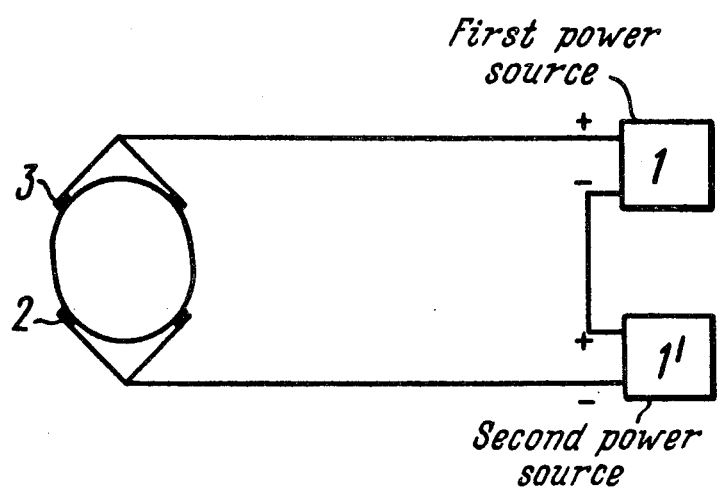

METHOD OF ELECTROANESTHESIA

The present invention relates generally to the art of medicine, more specifically to anesthesiology and has particular reference to a method of electroanesthesia.

A variety of electroanesthesia methods are known to make use of pulsed currents when performing surgical interventions. Thus, a method of electroanesthesia is known to involve induction anesthesia carried out with the use of ultrashort-action anesthetics, as well as forced pulmonary ventilation with a mixture of nitrous oxide and oxygen, while the depth of the anesthetic effect is changed by smoothly varying the repetition frequency of electric pulses applied through electrodes of which the cathode is arranged within the region of the forehead, while the anode is situated within the region of the neck under the mastoid processes. An optimum depth of anesthesia is obtained by varying the pulse repetition frequency at minimum voltage values.

A deeper anesthetic effect is attainable by increasing the output voltage. However, such a voltage rise is restricted by the development of the so-called "threshold sensations" beyond which pain sensations arise. That is why recourse should be had to as high nitrous oxide content of the gaseous-anesthetic mixture as 70 percent (cf., e.g., a paper by L. S. Persianinov et al. in the journal "Experimental Surgery and Anesthesia" No. 4, 1975, p. 74 published in Russian in the USSR), which may result in undesirable untoward effects on the one hand, and may call forth an increased consumption of the anesthetics involved. Thus, according to some evidence a total consumption muscle relaxants is to be increased by 15 to 20 percent compared to anesthesia with the use of a potent pharmacological anesthetic of the Fthorothan type. Moreover, on some occasions where the symptoms of inadequacy of the anesthesia appear, it is recommended that resort should be made not only to an increased pulse repetition frequency and a higher nitrogen content but also to an intravenous administration of analgesics, which is likewise undesirable and sometimes difficult to attain.

It is therefore an object of the present invention to provide such a method of electroanesthesia involving the use of pulsed currents that would ensure a deeper anesthetic effect without any increase in the consumption of relaxants and in the content of nitrous oxide in the inhaled mixture, as well as without administration of additional analgesics in the course of operation.

The aforesaid and other objects are accomplished due to the fact that applied to the region of the forehead and neck are stabilized voltage pulses of the same amplitude, the difference between the pulse repetition frequencies ranging within about 100 to about 200 Hz.

Such a method may be carried into effect with the use of frequency-controlled stabilized D.C. voltage sources interconnected in series and connected respectively to the region of the patient's neck and forehead.

It is expedient that provision should be made for the pulse repetition frequency in each of the aforesaid voltage sources to be within 1500 Hz so as to obtain a difference between the pulse repetition frequencies within about 100 to about 200 Hz, and that the same voltage amplitude should be set in every voltage source.

In what follows the present invention is illustrated in a detailed description of some specific embodiments thereof and the drawing enclosed, showing schematically the apparatus for carrying out the method of the present invention.

The herein-disclosed method may be carried into effect using power sources 1 and 1' that generate stabilized voltage pulses and have a means of smooth varying the pulse repetition frequency and length at constant and variable pulse ratio, by applying, say, an instrument as disclosed in U.S. Pat. No. 4,185,640 issued to E. M. Kastrubin et al. on Jan. 29, 1980 and cited herein by way of reference whereby said instruments is not described in detail in the present disclosure. Two of the aforesaid instruments must be had, interconnected in series, in order to carry into effect the method according to the present invention.

The method of the present invention is realized as follows. 30 to 40 minutes before the operation the patient is given premedication in keeping with the existing conventional preoperative treatment techniques which are the subject of common knowledge. The patient is admitted to the operating room, wherein a mask made of rubber strips with four electrodes 2 and 3 built thereinto is put on the patient's head. Two of the electrodes 3 are applied to the forehead as the cathode, while another two electrodes 2 are applied to the neck under the mastoid processes as the anode. In so doing use must be made of gauze pads composed of 15 to 20 gauze layers wetted in a 4 or 5 percent soda solution.

Then the current limiters are set simultaneously for an average current intensity of up to 2.5 mA in both of the power sources, while the pulse repetition frequency is adjusted to be within 800 to 1000 Hz in both of the stabilized voltage sources at a constant pulse ratio.

Next an additional constant component is increased simultaneously and within the same limits to 0.1 or 0.2 mA within an average current intensity, whereupon the output voltage of the both sources 1 and 1' is increased in synchronism until the patient feels tingling sensations under the electrodes applied to him, which corresponds to an increase in the average current intensity in the patient circuit to within 0.4 and 1.2 mA.

In 10 or 15 minutes induction anesthesia is carried out by administering ultrashort-action barbiturates in doses high enough to attain an optimum level of the induction anesthesia.

Intubation is carried out using a conventional dose of muscular relaxants, whereupon forced pulmonary ventilation begins with the use of a mixture of nitrous oxide and oxygen (2:1). Concurrently with the beginning of forced pulmonary ventilation there must be administered depolarizing relaxants of the Tubarin type.

Further on the voltage amplitude in both of the sources is minimized simultaneously, the pulse length is set within 0.15 to 0.20 ms and a constant pulse ratio is changed for a variable one, whereupon while simultaneously controlling the voltage amplitude of the both sources, one must increase the average current intensity in the patient circuit up to 1.0 or 2.5 mA, the additional component being eliminated from the circuit.

To provide optimum conditions for carrying out electroanesthesia without additional administration of relaxants and analgesics, use is made of a difference between the pulse repetition frequencies within 100 to 200 Hz.

Whenever the depth of impulse effect must be controlled, the amplitude of the both stabilized voltage sources is either decreased or increased in synchronism.

One must keep periodical watch for an adequate moisture of the gauze pads in the course of operation.

If necessary simultaneously variation of the average current intensity in the patient circuit may be carried out by synchronously regulating the limiters of the average current intensity, thus making possible increasing or decreasing the depth of impulse effect to suit individual features of the patient.

Numerous operations have been performed with the use of the proposed method, reports of some of these being cited hereinbelow. To take an example of practical application of the present method, let us consider a surgical intervention for adenocarcinoma of the corpus uteri in a patient aged 49, body weight 116 kg, affected by hypertensive disease.

Premedication has been given 30 to 40 minutes before the operation adhering to routine techniques with the exception of Atropine administration.

In the operating room immediate preparation for anesthesia has been made by the effect of pulsed currents. To this end a mask of four electrodes (two cathodes in the region of the forehead and two anodes in the region of the neck under the mastoid processes) has been connected to the two series-connected stabilized voltage sources provided in accordance with U.S. Pat. No. 4,185,640, whereupon a difference between the pulse repetition frequency has been adjusted within 100 to 200 Hz at a constant pulse ratio. Then the output voltage of both sources has been adjusted till appearing threshold sensations in the patient. Further on induction anesthesia has been effected by a 2.5 percent Hexenal (300 mg), Dityline (100 mg), as well intubation of the trachea, whereupon one of the voltage sources has been set for a variable pulse ratio, and the voltage has been brought to a level corresponding to an average current intensity of 2.5 mA. Then the patient has been connected to a forced pulmonary ventilation apparatus, and such ventilation has been carried out with a mixture of $N_2O$ and $O_2$ (2:1).

Muscle relaxation has been maintained following a single administration of 30 mg Tubarin in fractional doses not in excess of 7.5 mg. The operation has taken 5 hours to perform. Stable hemodynamics (150/90, and 140/80, pulse rate 72 beats per minute) has given evidence of an adequately deep anesthesia. At especially traumatic moments of operation the depth of the anesthetic effect has been increased by appropriately combining a constant and a variable pulse ratios. No analgesics, tranquilizers or hypotensive drugs have been administered to the patient in the course of operation.

Arousal of the patient has been accompanied by complete recovery of consciousness and restoration of reflex effects 1 or 2 minutes after stopping current supply.

To take another example, a similar anesthesia procedure has been carried out during a Wertheim's operation for adenocarcinoma of the corpus uteri in a patient aged 32, body weight 54 kg.

The operation has taken 5 hours 25 minutes to perform, the consumption of Tubarine being 52.5 mg, that of Dityline, 100 mg. Arousal of the patients has occurred 1 to 2 minutes after stopping current supply.

Practical application of the proposed method of electroanesthesia extends much the scope of uses of that kind of anesthesia, inasmuch as it makes possible considerable decreasing of the consumption of potent anesthetic or ruling out their use from standard schemes of anesthesia application, and enables anesthesia to be carried out in the course of operation of any duration without administering additional analgesics, increasing the consumption of relaxants, and increasing the concentration of nitrous oxide in the inhaled gaseous mixture.

While a preferred embodiment of the herein-proposed method of electroanesthesia has been described by us hereinbefore various changes or modifications may occur to those skilled in the art and these can be made without departing from the spirit and scope of the invention as defined in the claims to follow.

What we claim is:

1. A method of electroanesthesia of a patient, comprising conducting preliminary preoperative medicamentous preparation, conducing induction anesthesia, administering muscle relaxants, conducting intubation followed by forced pulmonary ventilation, and applying D.C. pulses involving an additional constant component with the help of electrodes placed in the region of the forehead and neck of the patient, said D.C. pulses being stabilized voltage pulses having the same amplitude and a difference between the repetition rates within a range of from about 100 Hz to about 200 Hz, the electrodes including cathodes applied within the region of the forehead, and anodes applied within the region of the neck, wherein, prior to conducting induction anesthesia, the patient is given a treatment with constant pulse ratio pulses applied for a period of about 20 minutes at a repetition frequency within a range of 800 Hz to 1000 Hz in combination with an additional constant component of from 0.1 mA to 0.2 mA, while increasing the average current intensity of the stabilized voltage in the patient circuit up to a range of about 0.4 mA to 1.2 mA.

2. A method of electroanesthesia of a patient, comprising conducting preliminary preoperative medicamentous preparation, conducing induction anesthesia, administering muscle relaxants, conducting intubation followed by forced pulmonary ventilation, and applying D.C. pulses involving an additional constant component with the help of electrodes placed in the region of the forehead and neck of the patient, said D.C. pulses being stabilized voltage pulses having the same amplitude and a difference between the repetition rates within a range of from about 100 Hz to about 200 Hz, the electrodes including cathodes applied within the region of the forehead, and anodes applied within the region of the neck, wherein the stabilized voltage pulses are derived from two series-connected D.C. sources.

3. A method as claimed in claim 2, wherein, after starting forced pulmonary ventilation, the voltage amplitude of the series-connected stabilized voltage sources is simultaneously minimized, and the pulse length is set to be within a range of 0.15 ms to 0.20 ms, whereupon the voltage amplitude of the stabilized voltage of the two series-connected D.C. sources is increased again until the current in the patient circuit rises to a range of 2 mA to 2.5 mA, and the pulses are applied at a variable pulse ratio.

4. A method a claimed in any one of claims 1, 2 or 3 to conducting the induction anesthesia, the patient is given a treatment with constant pulse ratio pulses applied for a period of about 20 minutes at a pulse repetition frequency within a range of 800 Hz to 1000 Hz in combination with an additional d-c component having a current range of 0.1–0.2 mA while increasing the average current intensity of the stabilized voltage in the patient circuit to a range of about 0.4–1.2 mA.

* * * * *